US012622608B2

(12) United States Patent
Tsubouchi

(10) Patent No.: US 12,622,608 B2
(45) Date of Patent: May 12, 2026

(54) AQUEOUS BUFFER PROTECTION SYSTEM FOR BIOSENSORS

(71) Applicant: TERUMO CARDIOVASCULAR SYSTEMS CORPORATION, Ann Arbor, MI (US)

(72) Inventor: Takeshi Tsubouchi, Dexter, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 869 days.

(21) Appl. No.: 17/875,903

(22) Filed: Jul. 28, 2022

(65) Prior Publication Data

US 2022/0378336 A1     Dec. 1, 2022

Related U.S. Application Data

(63) Continuation of application No. PCT/US2021/018148, filed on Feb. 16, 2021.

(Continued)

(51) Int. Cl.
*A61B 5/00* (2006.01)
*A61B 5/145* (2006.01)

(52) U.S. Cl.
CPC ...... *A61B 5/14503* (2013.01); *A61B 5/14517* (2013.01); *A61B 5/14532* (2013.01)

(58) Field of Classification Search
None
See application file for complete search history.

(56) References Cited

U.S. PATENT DOCUMENTS

| | | |
|---|---|---|
| 8,649,836 B2 | 2/2014 | Shimizu et al. |
| 2010/0137778 A1 | 6/2010 | Kunjan et al. |

(Continued)

FOREIGN PATENT DOCUMENTS

| | | |
|---|---|---|
| EP | 0276535 B1 | 12/1992 |
| JP | 2000-505675 A | 5/2000 |

(Continued)

OTHER PUBLICATIONS

International Search Report, Written Opinion, PCT/US2021/018148, Apr. 28, 2021.

(Continued)

*Primary Examiner* — Niketa Patel
*Assistant Examiner* — Anant A Gupta
(74) *Attorney, Agent, or Firm* — Fish & Richardson P.C.

(57) ABSTRACT
Usable life of a biosensor life is extended while keeping the sensing system enclosed and minimizing the introduction of flushing solutions into a measurement line (e.g., a blood vessel) of a fluid system, such as a human blood vessel, a nutritional fluid line in a tissue cultivation system, or a circulation system in an organ preservation system. A catheter, tube, or other lumen contains the active biosensor. One end of the lumen is introduced to the target fluid, and the other end is connected to a supply of a buffer solution (e.g., heparinized saline solution). By advancing the buffer solution along the lumen, the biological fluid (e.g., blood) can be purged from the area around the sensor material to halt any reactions. When a measurement is desired, then the buffer solution is withdrawn (e.g., suctioned) back into the supply so that the biological fluid enters and contacts the sensor material.

8 Claims, 8 Drawing Sheets

Related U.S. Application Data

(60) Provisional application No. 63/031,605, filed on May 29, 2020, provisional application No. 62/980,500, filed on Feb. 24, 2020.

(56) References Cited

U.S. PATENT DOCUMENTS

| | | | |
|---|---|---|---|
| 2010/0252430 A1* | 10/2010 | Say | C12Q 1/004 |
| | | | 204/415 |
| 2011/0184258 A1 | 7/2011 | Stafford | |
| 2016/0024455 A1 | 1/2016 | Nankervis | |
| 2016/0073940 A1* | 3/2016 | Winkelman | A61B 5/14865 |
| | | | 600/365 |
| 2016/0374612 A9 | 12/2016 | Hulvershorn et al. | |
| 2017/0332953 A1 | 11/2017 | Say | |
| 2019/0282143 A1* | 9/2019 | Kamath | A61B 5/1473 |

FOREIGN PATENT DOCUMENTS

| | | | |
|---|---|---|---|
| WO | WO 2008042625 A2 | 4/2008 | |
| WO | 2008112845 A2 | 9/2008 | |

OTHER PUBLICATIONS

The extended European search report, Application No. PCT/US2021018148, dated Dec. 21, 2023.

* cited by examiner

45

46

Optic Fiber
Sensor

Flourescent
Dye

To
Controller

Interface 61

50

57    58    60

A

B

C

53

54    56    55

Specimen 52    51

AQUEOUS BUFFER PROTECTION SYSTEM FOR BIOSENSORS

CROSS REFERENCE TO RELATED APPLICATIONS

This application is a continuation of PCT Application No. PCT/US2021/018148, filed Feb. 16, 2021, based on and claiming priority to U.S. Provisional Application No. 62/980,500, filed Feb. 24, 2020, and to U.S. Provisional Application No. 63/031,605, filed May 29, 2020, all of which are incorporated herein by reference in their entirety.

BACKGROUND OF THE INVENTION

The present invention relates in general to sensors (e.g., biosensors) for monitoring biological fluids such as blood, and, more specifically, to a protection system for prolonging a useful lifetime of such biosensors.

Biosensors can be used for measuring chemicals, other substances, and various properties of a target biological fluid such as blood. The measured quantities can include concentration of gases, proteins, pH, and other parameters of biological fluids. Some types of biosensors may use enzymes or other reactive materials to contact the fluid when making a measurement. During the time they are exposed to the biological fluid, the reaction can eventually degrade the sensor materials such that the sensor becomes less effective over time. Besides degradation of sensor materials, a buildup of protein layers or clotted blood around the sensor material during exposure can also reduce effectiveness of the sensor over time.

An example of a biosensor includes an enzyme-based amperometric glucose measurement sensor or a blood parameter monitoring sensor such as the CDI® blood parameter monitoring system which is available from Terumo Cardiovascular Systems Corporation of Ann Arbor, Michigan The CDI® sensor uses optical fluorescence, reflectance, and/or other sensing elements to measure blood parameters including pH, $pCO_2$, $pO_2$, K+, $SO_2$, hemoglobin, hematocrit, and others in blood during cardiopulmonary bypass. Although continuous measurement may be desirable in some cases, many parameters change slowly such that continuous measurement is not required. Instead, measurements can be made periodically (especially during long duration monitoring).

SUMMARY OF THE INVENTION

An objective of the invention is to extend sensor life while keeping the sensing system enclosed (e.g., free from outside contamination) while minimizing the introduction of flushing solutions into a measurement line (e.g., a blood vessel) of a fluid system. The fluid system targeted for measurement can include a human vessel, a nutritional fluid line in a tissue cultivation system, a circulation system in an organ preservation system, and others.

The invention utilizes a catheter, tube, or other lumen to contain the active biosensor. One end of the lumen is introduced to the target fluid, and the other end is connected to a supply of a buffer solution (e.g., heparinized saline solution). By advancing the buffer solution along the lumen, the biological fluid (e.g., blood) can be purged from the area around the sensor material to halt any reactions. When a measurement is desired, then the buffer solution is withdrawn (e.g., suctioned) back into the supply so that the biological fluid enters the lumen and contacts the sensor material.

DETAILED DESCRIPTION OF PREFERRED EMBODIMENTS

Figures 1, 2:
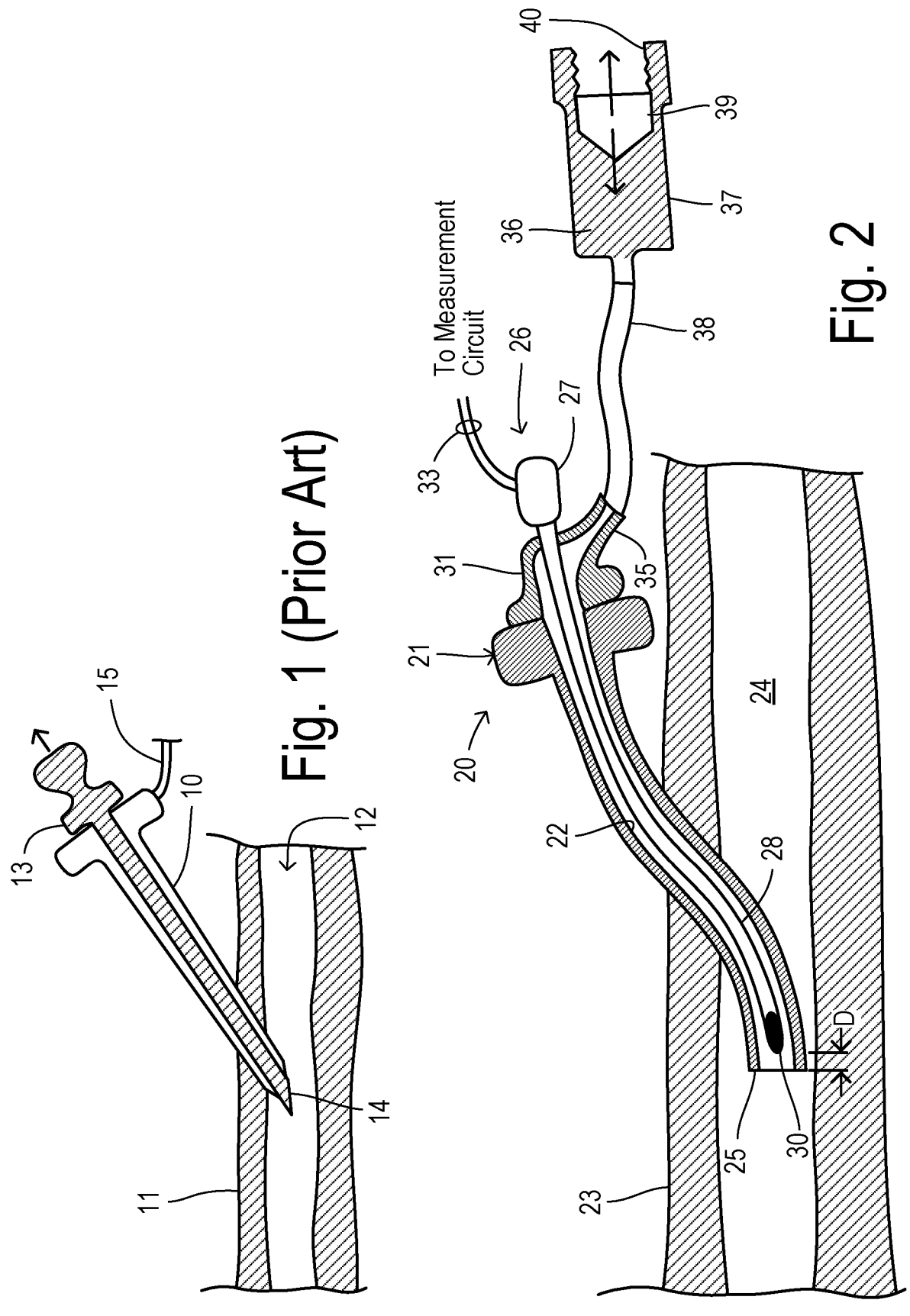
FIG. 1 is a cross-sectional view of a conventional needle sensor.
FIG. 2 is a cross-sectional view of a modified needle sensor according to one embodiment of the invention.

FIG. 1 shows a conventional needle sensor system with a hollow injection needle 10 having a tip penetrating a blood vessel 11 into a bloodstream 12. A sensor 13 has a sensing tip 14 penetrating bloodstream 12 and providing a sensor output signal over wires 15 to a measurement circuit. Once the system is implanted in a patient, sensor 13 remains in place and is continuously exposed to bloodstream 12.

In a first embodiment of the invention shown in FIG. 2, a sensing system 20 has an implantation catheter 21 with a central lumen 22. Catheter 20 penetrates a blood vessel 23 into a bloodstream 24. Catheter 21 has an open distal end 25. A sensor element 26 has a head end 27, an elongated body 28, and a tip 30. Elongated body 28 passes through a fitting 31 in a sealed manner. Fitting 31 encloses and seals a proximal end of catheter 21 when sensor element 26 is attached. The lengths of body 28 and catheter 21 are configured such that tip 30 remains in internal lumen 22 and is spaced from distal end 25 by a distance D. Signal wires 33 carry a sensor output signal to a measurement circuit from sensor head 27.

Fitting 31 includes an inlet 35 for receiving a buffer solution 36 from a reservoir 37 via a tube 38. Buffer solution 36 can be comprised of water or saline solution (e.g., Ringer's solution) and may include an anticoagulant such as Heparin. Reservoir 37 has a volume sufficient to provide buffer solution to fill lumen 22. A plunger 39 is mounted for reciprocating longitudinal motion inside reservoir 37 in order to selectably pump buffer solution into lumen 22 (e.g., toward distal tip 25) by advancing plunger 39 or to selectably withdraw buffer solution from lumen 22 (e.g., into reservoir 37) by retracting plunger 39. Withdrawing buffer solution from lumen 22 draws blood from bloodstream 24 into lumen 22 by suction, in order to bathe sensor tip 30 with blood for making a desired measurement. Plunger 39 may be threaded or connected to a shaft or other component which is threaded complementary to a threaded inside diameter 40 of reservoir 37 in order to obtain longitudinal motion by rotating plunger 39, for example.

Figure 3:
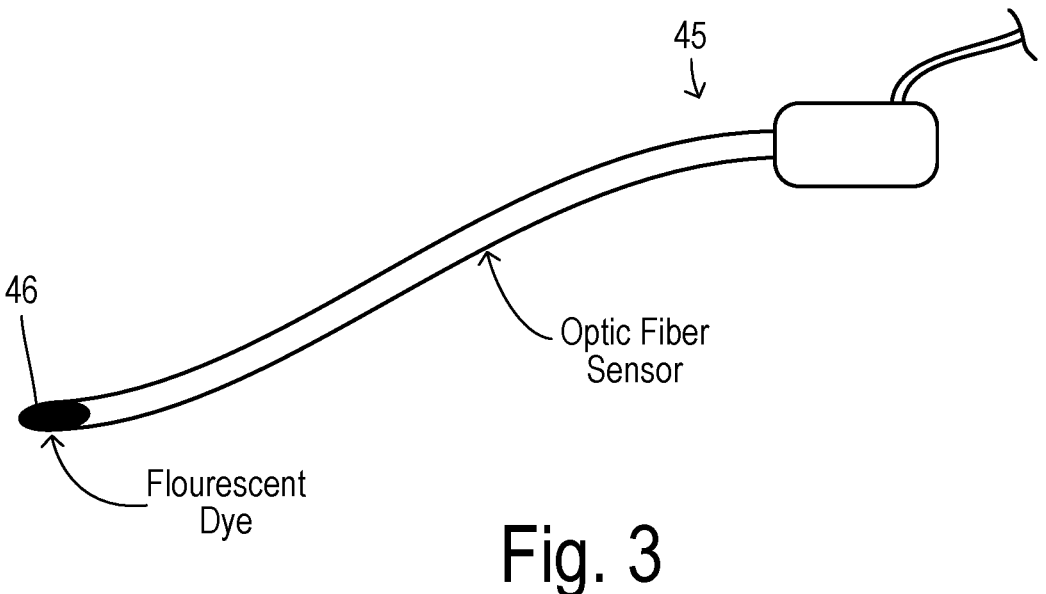
FIG. 3 is a side view of an alternative sensor element useful in the needle sensor of FIG. 2.

Sensor element 26 may be comprised of a microsensor with an enzyme-modified electrode. Alternatively, a fiber optic microsensor 45 can be used as shown in FIG. 3. A fluorescent dye tip 46 produces light when stimulated by a light source via the optical fiber which varies according to particular parameters of the target fluid being monitored. Tip 46 is at a position that results in it being protected within the catheter lumen when sensor 45 is installed in the sensing system of FIG. 2.

Figure 4:
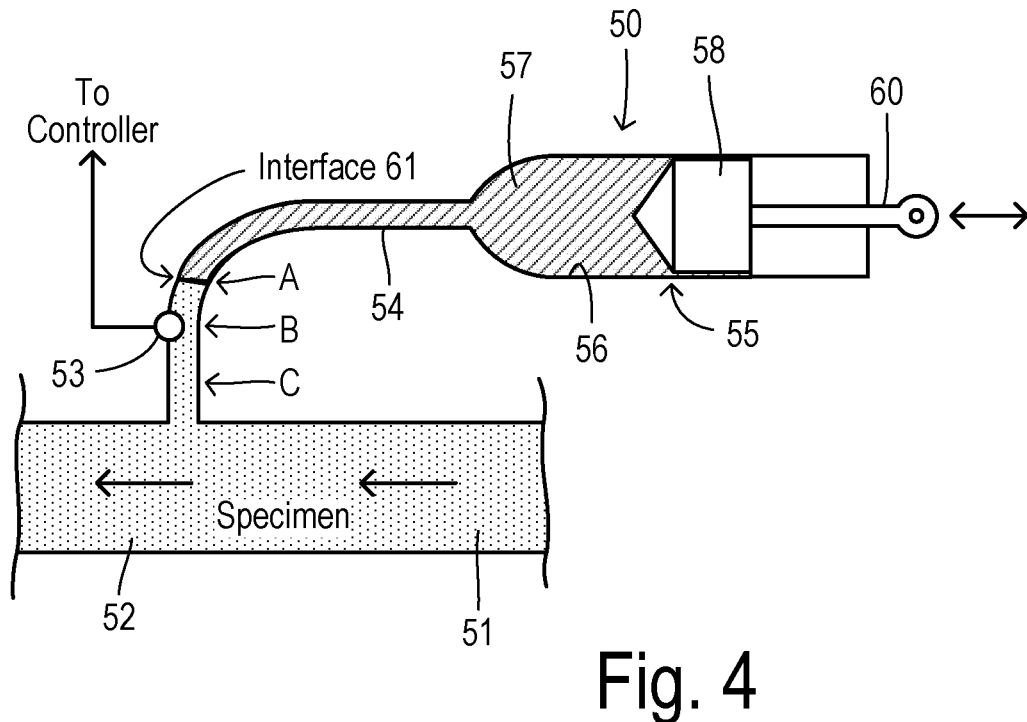
FIG. 4 is a schematic view of another embodiment of the invention.

FIG. 4 shows another embodiment of a sensor system 50 for measuring a property of a specimen fluid 51 in a conduit 52 (e.g., a blood vessel such as an artery, or a tissue cultivation system nutrition line). An enzyme-based or other type of sensor 53 is mounted in a narrow tube 54 between conduit 52 and a buffer solution supply unit 55. Sensor 53 is arranged to be exposed to fluid within tube 54, and provides an electrical output signal to a controller or other measurement circuit (not shown). Supply unit 55 has a reservoir chamber 56 containing a buffer solution 57. Unit 55 preferably has a cylindrical shape with a plunger 58 being longitudinally movable while maintaining a fluid seal around its periphery. A handle 60 can be manipulated to move back and forth to control a flow of buffer solution 57 in either direction through tube 54.

Tube 54 is sufficiently narrow to minimize mixing between buffer solution 57 and specimen fluid 51 along their interface 61. By advancing plunger 58 into reservoir chamber 56, interface 61 can be advanced sequentially along locations A, B, and C. In location A, sensor 53 is exposed to specimen fluid 51 and measurements can be taken. In location C, sensor 53 is immersed in buffer solution 57 so that degradation of the sensor materials is inhibited. Thus, by appropriately moving plunger 58 (e.g., using a servomechanism or manually), measurements can be obtained at a desired frequency while minimizing the exposure of the sensor material and extending the useful lifetime of the sensor.

Figure 5:
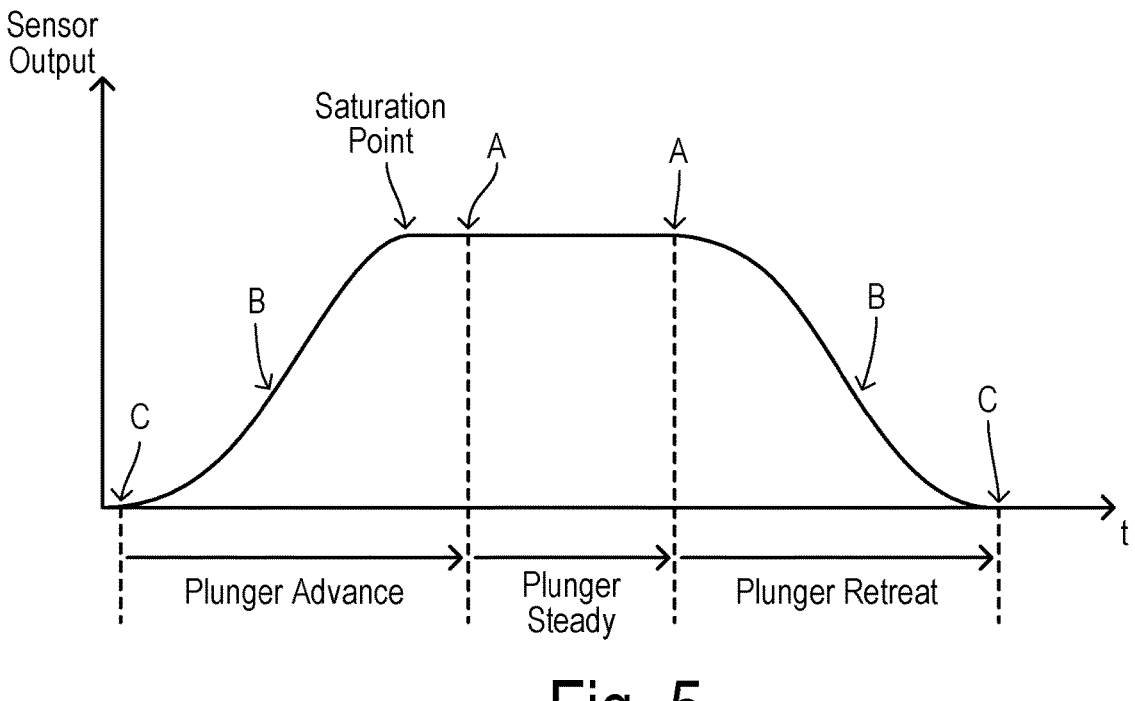
FIG. 5 is a graph illustrating a sensor output signal over a measurement cycle.

FIG. 5 illustrates a preferred method of controlling the plunger according to desired sampling times. At an initial time in the graph of FIG. 5, the plunger may be in an advanced position so that the interface between buffer solution and the specimen fluid is at location C (i.e., the sensor is contacted by buffer solution). The plunger is gradually retracted through location B resulting in exposure of the sensor to the specimen fluid and causing an increase in the sensor output. After the interface progresses past the sensor toward location A, the sensor output eventually reaches a saturation point where it levels off. Once the saturation point is reached (e.g., at location A) then the plunger is held steady during a desired measurement interval. Depending upon mixing of fluids at the interface and other factors that occur over time, the leveling off may not occur until after a progressively greater retraction of the plunger is obtained after multiple measurement cycles have been performed. By waiting for the detection of the saturation point, the invention ensures that an undiluted sample of the specimen fluid has reached the sensor.

At the end of a sampling time, the plunger is advanced to push the interface through location B and back to location C. The sensor output can be monitored during the plunger advancement. Once the sensor output disappears, then the plunger advancement can be stopped.

Figure 6:
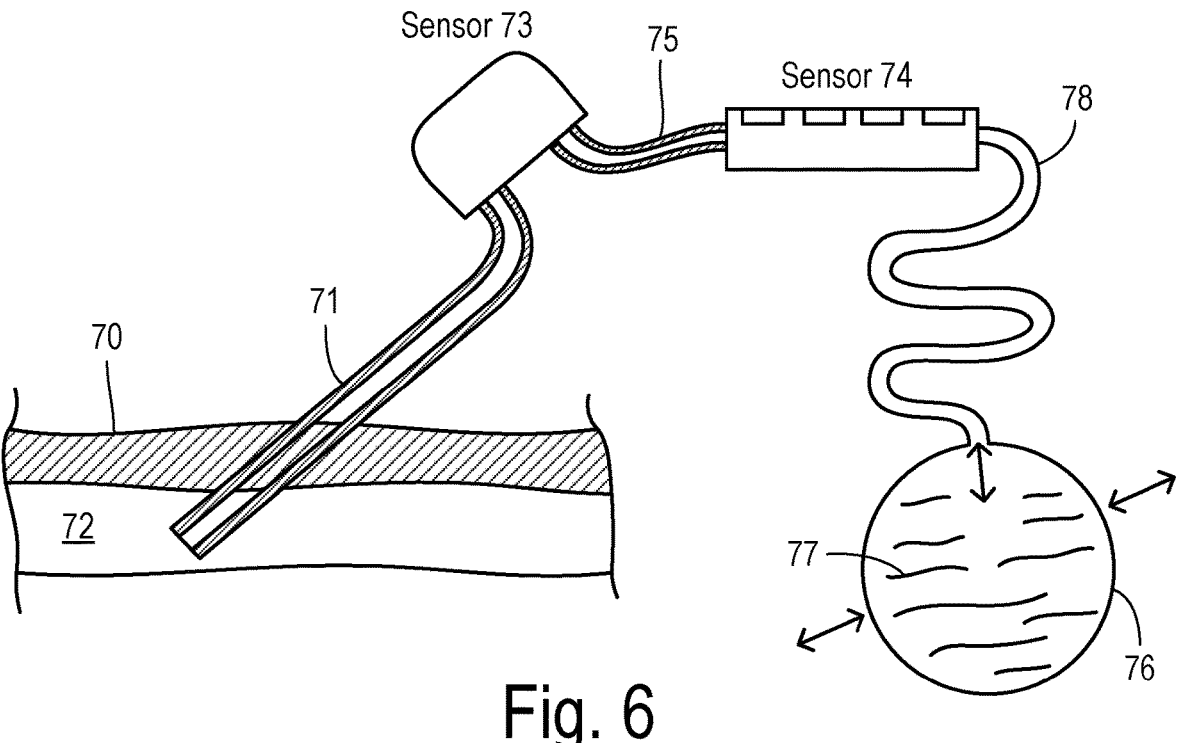
FIG. 6 depicts another embodiment of the invention with multiple sensors along a series of tubing.

FIG. 6 shows another embodiment wherein one or more sensors are linked to the specimen fluid by one or more sections of tubing. A blood vessel 70 or other conduit of a specimen fluid 72 is penetrated by a catheter or needle 71 which can convey fluid 72 to a sensor 73. Sensor 73 is an in-line sensor that further passes fluid 72 to another in-line sensor 74 via tubing 75. A tubing section 78 connects sensor 74 to a supply unit 76 filled with a buffer solution 77. Tubing section 78 is a long line in order to reduce contamination and/or mixing. Compressing (i.e., squeezing) unit 76 advances buffer solution 77 through sensors 73 and 74, while decompression (i.e., releasing) of unit 76 advances specimen fluid 72 into sensors 73 and 74 Unit 76 may be a resilient, elastomeric bulb which naturally re-expands after squeezing.

Figure 7:
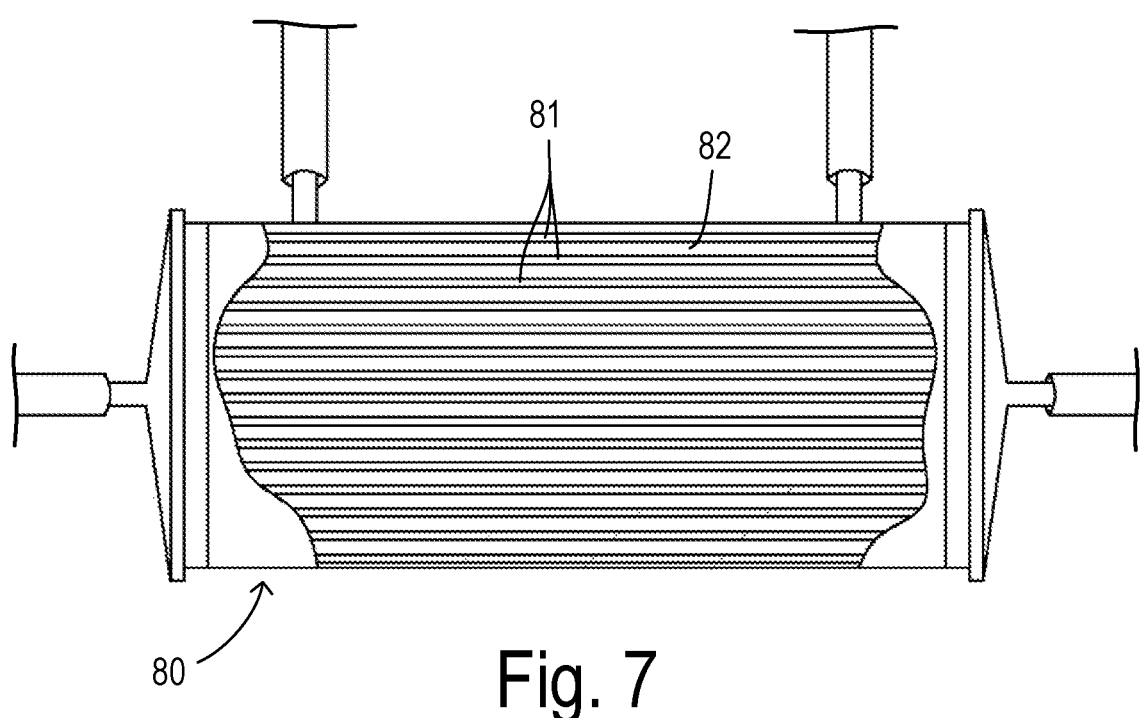
FIG. 7 depicts a hollow fiber system portion of a base tissue cultivation system.
Figure 8:
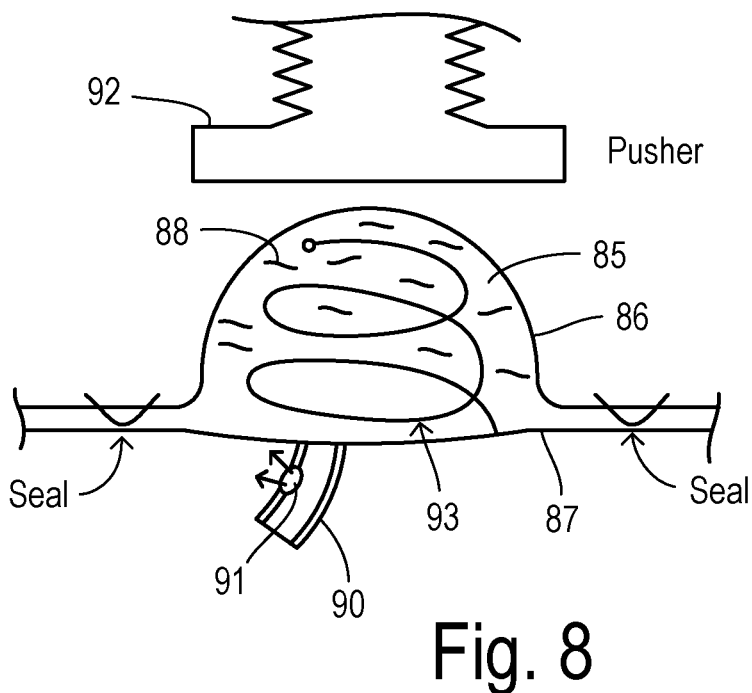
FIG. 8 shows a sensor and protection system adapted to obtain measurements within the hollow fiber of the tissue cultivation system of FIG. 7.

FIG. 7 shows a hollow fiber unit 80 (e.g., a bioreactor) having a plurality of hollow fibers 81 within an extra-capillary space 82. In some embodiments, cells being cultivated can be located in space 82, while a nutrient supply is circulated through fibers 81. A tissue cultivation system of this type is described in U.S. patent application publication US2016/0024455A1, which is incorporated herein by reference. Chemical monitoring may be desired for at least one of the cellular components or the nutrient supply. The nutrient fluids may likewise breakdown the materials in various sensors that may be used to characterize the states of the fluids. FIG. 8 shows an embodiment of the invention adapted for use in a bioreactor. A chamber 85 is formed between pliable sheets 86 and 87 which are sealed together around a periphery of chamber 85. Chamber 85 is filled with a buffer solution 88. Sheet 87 is penetrated by a catheter or needle 90 which is adapted for emplacement into a hollow fiber or an internal chamber of the tissue cultivation apparatus. A sensor 91 is mounted within catheter 90 and provides sensor output signals to a measurement circuit (not shown). A pusher 92 can be activated in order to push down on a coil spring 93 installed in chamber 85, so that chamber 85 is compressed and buffer solution 88 advanced along catheter 90.

In addition to extending the service lifetime of a single sensor or combination of different sensors, some embodiments of the invention can obtain even longer extensions of the service life of a sensing system by incorporating tandem sensors (e.g., sensors of the same type) connected redundantly in a serial arrangement that exposes only a first sensor until performance of the first sensor is degraded and then permits the first sensor and a second sensor to be exposed while utilizing sensor signals of only the second sensor. Additional sensors in series can be utilized in the same manner wherein a third sensor does not become exposed to the target fluid until the second sensor becomes degraded, and so on. As a result, the sensing of a target parameter can be conducted over a much longer time without requiring interruption of a procedure or replacement of any devices or fluid conduits. The extended duration of usable sensing time enables the use of a higher sampling frequency (i.e., less time between successive samples) to better characterize the sampled parameter and respond more quickly to anomalies.

Figure 9:
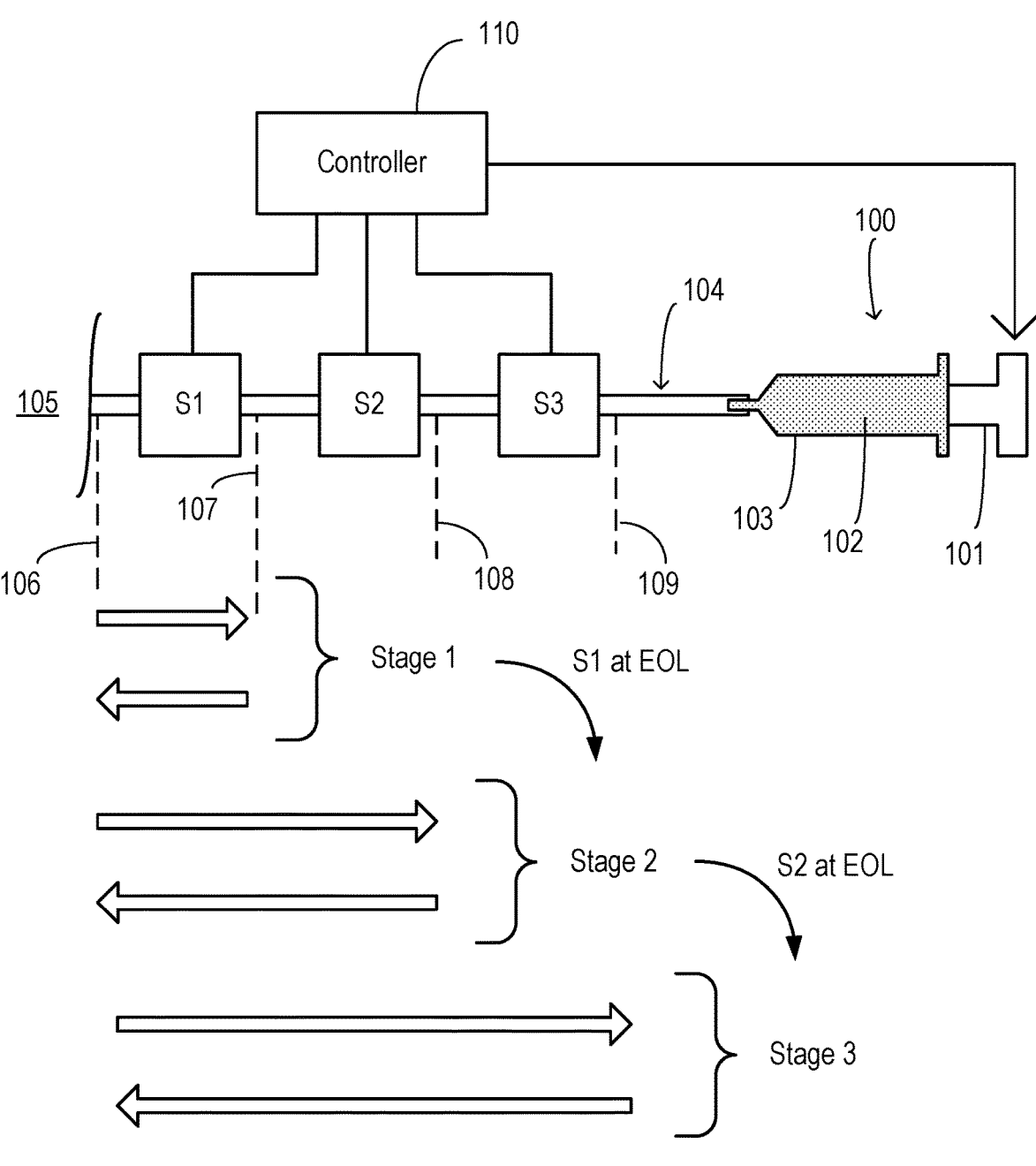
FIG. 9 shows an embodiment having tandem sensors in series along a fluid path to be operated in stages.

FIG. 9 shows a biosensor system for measuring a property of a specimen fluid 105 in a body (e.g., blood vessel) or a tissue cultivation system. A buffer solution supply unit 100 has a reservoir chamber 103 containing a buffer solution 102. Unit 100 preferably has a cylindrical shape with a plunger 101 being longitudinally movable while maintaining a fluid seal around its periphery. Plunger 101 may include a handle coupled to an actuator (e.g., a linear motor, not shown) to move plunger 101 back and forth to control a flow of buffer solution 102 in either direction through a conduit or tube 104. The actuator may be controlled by a controller 110 (e.g., a microcontroller). Tandem sensors S1, S2, and S3 are substantially identical sensors (e.g., enzyme-based) coupled in series along tube 104 for controlled exposure to either buffer solution 102 or specimen fluid 105. Each section of tube 104 is relatively narrow (i.e., the cross-sectional diameter is much less than the tube length) in order to minimize mixing between specimen fluid 105 and buffer solution 102 at a fluid interface that is initially at a location 106 where tube 104 enters the body (e.g., blood vessel). When sampling first begins (i.e., all sensors have a maximum remaining lifetime), specimen fluid 105 is delivered only to sensor S1 by retracting plunger 101 by a distance that causes the fluid interface to retract to location 107—referred to as a Stage 1 operation. During Stage 1, controller 110 exchanges electrical signals with sensor S1 (e.g., drive signals to S1 and measurement signals back from S1). At the end of obtaining a sample, plunger 101 is restored to a forward position so that the fluid interface returns to location 106. Stage 1 operation continues for the useful lifetime of sensor S1. During Stage 1, sensors S2 and S3 are never exposed to specimen fluid 105, only to buffer solution 102, and controller 110 ignores sensors S2 and S3. At an End Of Life (EOL) of sensor S1, the sampling enters a Stage 2 operation wherein specimen fluid 105 is delivered to sensors S1 and S2 by retracting plunger 101 by a distance that causes the fluid interface to retract to location 108 in tube 104. In Stage 2, controller 110 exchanges signals with sensor S2 and ignores sensors S1 and S3. At the EOL of sensor S2, the sampling enters a Stage 3 operation wherein specimen fluid 105 is delivered to sensors S1, S2, and S3 by retracting plunger 101 by a distance that causes the fluid interface to retract to location 109 in tube 104. In Stage 3, controller 110 exchanges signals with sensor S3 and ignores sensors S1 and S2. Between measurements in Stages 2 and 3, the fluid interface is preferably returned to location 106, but could alternatively just be returned to a location that restores buffer solution to the sensor that is then being used to obtain measurements.

Figure 10:
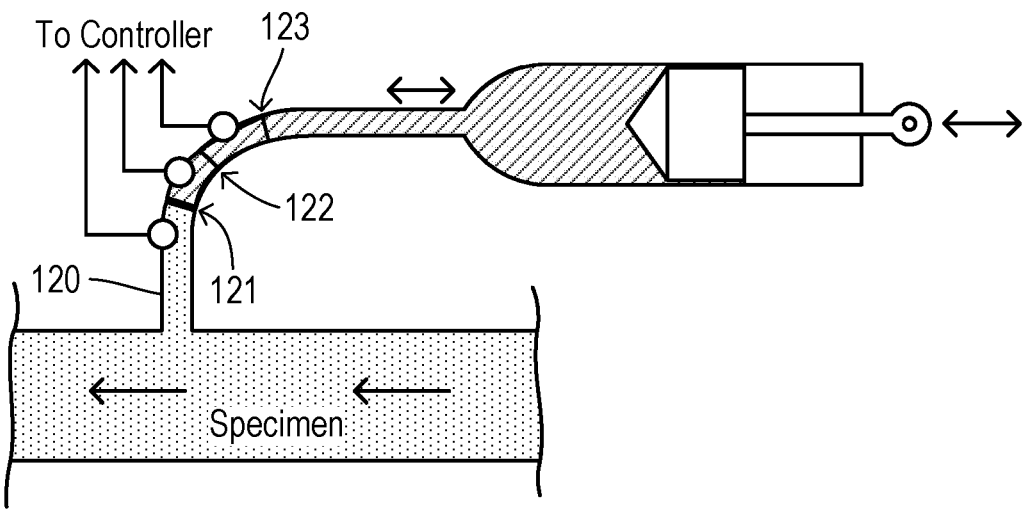
FIG. 10 depicts another embodiment with tandem sensors.

FIG. 10 shows another tandem embodiment wherein a tube 120 has successive sensors penetrating tube 120 at respective positions along the length of tube 120. Tube 120 is sufficiently narrow to minimize mixing between buffer solution and specimen fluid as a fluid interface is moved to various locations 121, 122, and 123 between successive sensors so that each sensor is used in a respective stage of operation.

Figure 11:
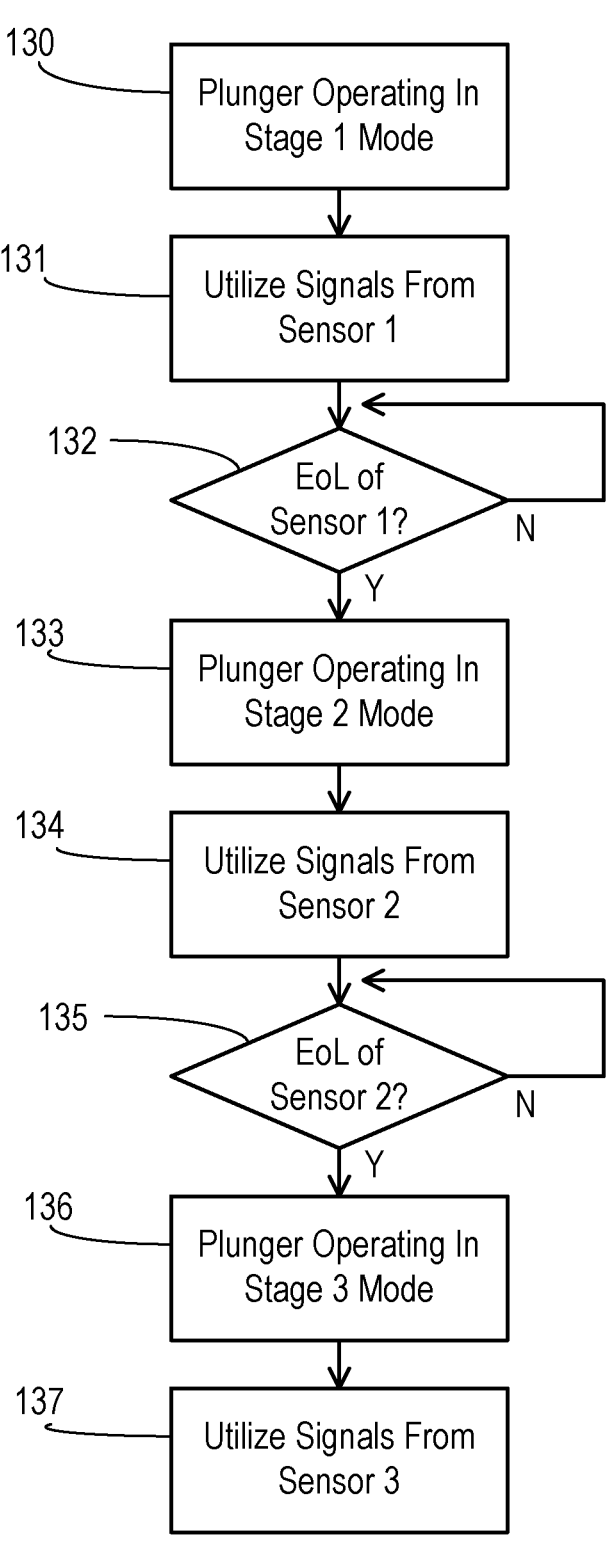
FIG. 11 is a flowchart showing one preferred method for operating tandem sensors.

A preferred method of the invention is shown in FIG. 11 wherein the plunger is operating in Stage 1 mode in step 130. In step 131, the controller utilizes signals from sensor S1. A check is performed in step 132 to determine whether sensor S1 has reached an end of life (EOL) condition. The check can be based on the number of measurement cycles performed (compared to a threshold count) and/or accumulated measurement time (compared to a predetermined time period) during which sensor S1 has been exposed to the specimen fluid. Alternatively, the check can be based on analysis of the sensor signals performed by the controller to detect when measurement performance has degraded. If the EOL of sensor S1 is not reached then the use of Stage 1 continues and the EOL condition of sensor S1 is continuously monitored in step 132.

Once the EOL of sensor S1 is reached, then the plunger begins operating in Stage 2 mode in step 133. The controller switches over to utilizing sensor signals from sensor S2 in step 134. The EOL is checked for sensor S2 in step 135. Once the EOL for sensor S2 is reached, then the plunger operates in Stage 3 mode in step 136 and the controller switches over to utilizing signals from sensor S3 in step 137.

In a further aspect of the invention, a degradation state of a sensor can be monitored throughout its useful lifetime. Using the degradation state of the sensor, an ongoing calibration of measurements is used to compensate for measurement errors that otherwise affect conventional devices.

Since there is very little mixing between the buffer solution and the target fluid, the composition of the buffer solution is substantially stable during usage. A small but measurable amount of a target chemical being measured by the sensor(s) may be added to the buffer solution—preferably at an accurately controlled concentration. The amount of target chemical can be made sufficiently small that very little degradation of the sensor occurs, even when contact is made with the sensor over long periods of time. Thus, a predetermined calibration concentration of the target substance is added, wherein the calibration concentration is less than a range of a range of expected concentration of the target substance to be encountered in the target fluid. When degradation does occur as a result of exposure to the target fluid during an accumulation of measurements of the concentration in the target fluid, then the measured concentration in the buffer solution will also degrade. Since the actual concentration in the buffer solution is known, the difference between the degraded measurements for the buffer solution and the known concentration can be used to determine the extent of degradation and to compensate the measured concentration for the target fluid.

For example, a sensor for monitoring Lactate in blood (e.g., to detect lack of oxygen and/or organ failure during a surgical procedure) may need to measure Lactate concentration ranging from 30 to 50 mmol/L. The sensor can be comprised of the CDT® blood parameter monitoring system mentioned above or other commercially available sensors. By adding Lactate to the buffer solution at a concentration of only 5 mmol/L, the chemicals (e.g., photo-reactive dyes) of the sensor will not significantly degrade. During cyclic exposure to higher levels of Lactate in the target fluid, however, the sensor will degrade which results in lower measured values for the Lactate concentration. Consequently, measurement values that are taken for the buffer solution (between measurement periods for the target fluid) could decrease down to 4 or 3 mmol/L and the decrease could be used to detect and/or compensate for sensor degradation.

Figure 12:
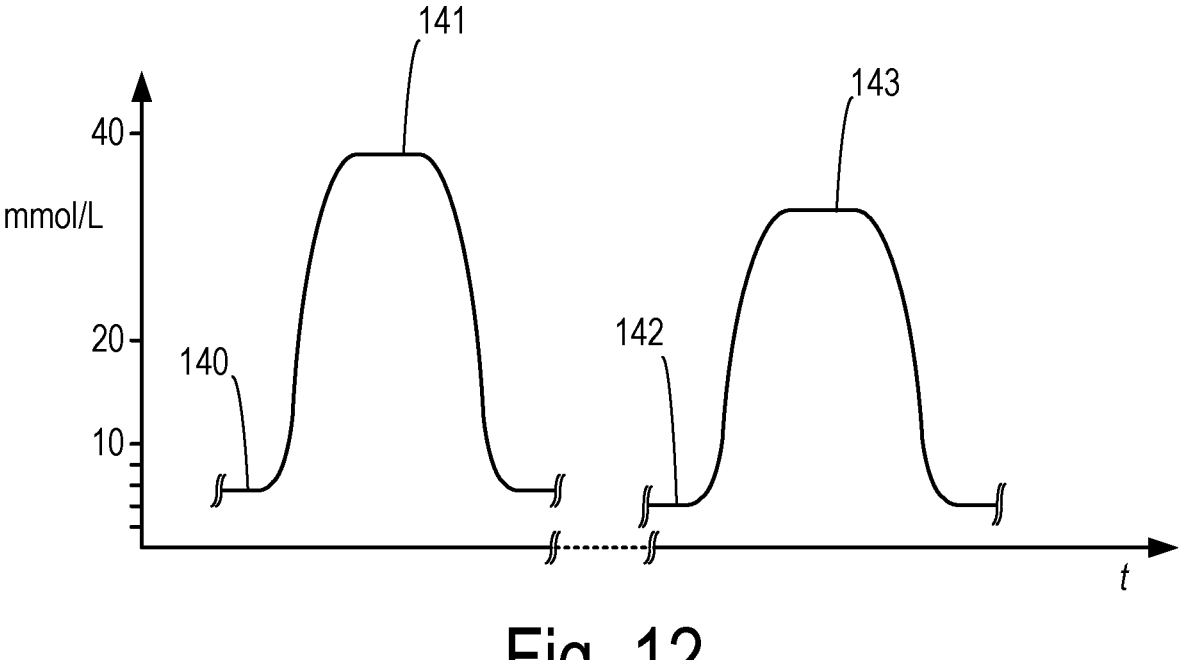
FIG. 12 is a graph showing measured sensor values for a target parameter over time, in which sensor degradation results in lowered sensitivity to the target parameter.

As shown in FIG. 12, measured values from a sensor may degrade over time. A baseline value 140 is initially measured during exposure to the buffer solution at about the known predetermined value of 5.0 mmol/L. The buffer solution is withdrawn from the sensor so that it becomes exposed to the target fluid. After a transition period, a measured value 141 is obtained for the target. Thereafter, the buffer solution is advanced over the sensor during quiescent periods and retracted during measurement periods to expose the sensor to the target fluid. The sensor degrades during the measurement periods due to the exposure to high concentrations of the target substance. During quiescent periods, sensor measurements are periodically obtained for comparison to the known value. At a later time (once there has been an onset of degradation), a measured value 142 obtained during a quiescent period has an erroneous value of about 3.0 mmol/L. The drop in the measured value quantifies the amount of degradation that has taken place. A subsequent measured value 143 obtained for the target fluid is degraded by the same amount. The difference between values 140 and 142 identifies a correction that can be applied to measured value 143 to compensate for the sensor degradation.

Figure 13:
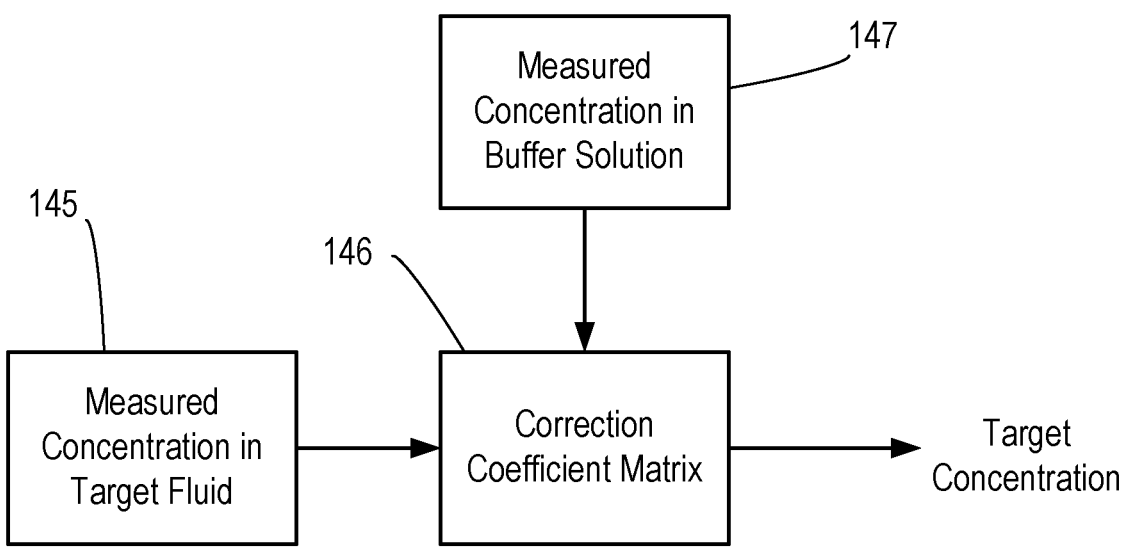
FIG. 13 is a block diagram showing compensation of sensor measurements based on inclusion of a known low concentration of the target parameter in the buffer solution.

As shown in FIG. 13, a measured concentration value 145 obtained for the target fluid is input to a correction coefficient matrix 146. Matrix 146 may be comprised of empirically derived correction coefficients which compensate for changes in sensor outputs at various levels of degradation. Matrix 146 could alternatively be comprised of an equation or formula. For example, for a 10% drop in the measured buffer concentration, the measured target fluid concentration could be multiplied by 1.1.

A most recent measured concentration value 147 for the buffer solution is input to matrix 146 to identify the proper coefficients to be applied. Based on the selected coefficients, matrix 146 outputs a measured target concentration having an improved accuracy.

Using the quiescent measurements, the end-of-life condition for any particular sensor can be detected. When the drop in detected values for a target substance in the buffer solution drop below a threshold, then the particular sensor can no longer be relied on. Then a next one of the tandem sensors is used, or if no other sensors are available then an error message can be generated to inform the user. For example, for a sensor system measuring glucose and having a glucose added to the buffer solution at a concentration of 5 mol/L, if the detected amount of glucose during the quiescent period drops below 3 mol/L then the sensor may be considered to have reached its end-of-life.

Figure 14:
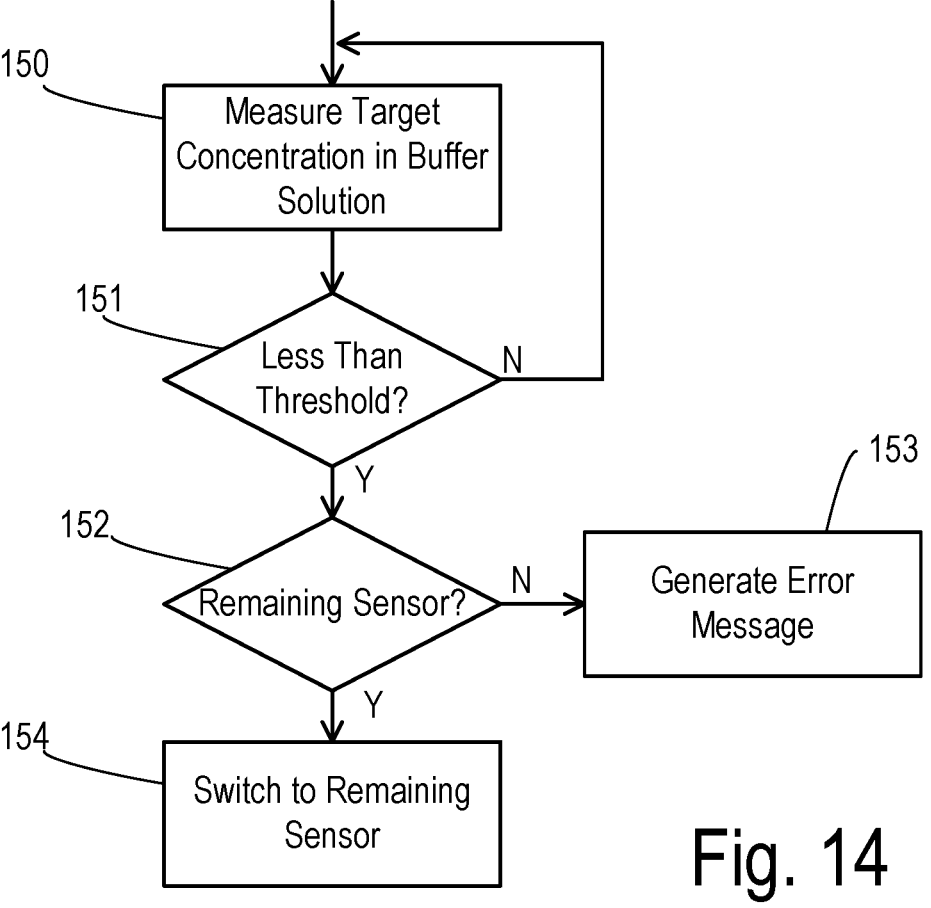
FIG. 14 is a flowchart showing a method for detecting end-of-life of an individual sensor and for initiating a switchover to a new sensor in a group of tandem sensors.

FIG. 14 shows a corresponding method wherein a concentration of the target substance in the buffer solution is measured in step 150. A check is performed in step 151 to determine whether the measured concentration is less than a threshold. The threshold is chosen to be indicative of a level of degradation beyond which the sensor is no longer usable. If the measured concentration is not less than the threshold, then a return is made to step 150 to repeat the check at a later time. If the measured concentration is less than the threshold, the a check is performed in step 152 to determine whether there is another sensor remaining which has not yet been exposed to the biological fluid (e.g., blood). If there is no remaining sensor (e.g., there are no tandem sensors, or the last tandem sensor has been used up), then an error message is generated in step 153. Otherwise, a switch is made to the remaining sensor which still possesses a useful remaining life. Thereafter, degradation of the newly selected sensor can be monitored by returning to step 150.

What is claimed is:

1. A biosensor system comprising:
   a conduit with an inner lumen with a first end for receiving a target biological fluid and a second end;
   a sensor coupled to the inner lumen remotely from a source of the target biological fluid, the sensor configured to detect a target substance; and
   a supply unit for a buffer solution coupled to the inner lumen, the buffer solution comprising a predetermined concentration of the target substance,
   wherein the supply unit includes a mechanism for advancing the buffer solution along the inner lumen so that the target biological fluid can be purged from an area around the sensor, wherein, when a measurement is desired, the buffer solution is withdrawn into the supply unit so that the target biological fluid enters the inner lumen and contacts the sensor, and
   wherein a measurement of the target substance in the buffer solution identifies an end-of-life of the sensor when the measurement is less than a threshold.

2. The biosensor system of claim 1 wherein the conduit is comprised of an implantation catheter configured to penetrate a blood vessel, and wherein the target biological fluid is comprised of blood.

3. The biosensor system of claim 1 wherein the buffer solution is comprised of a saline solution.

4. The biosensor system of claim 1 wherein the supply unit includes a reservoir for storing the buffer solution, and wherein the mechanism is comprised of a plunger mounted for reciprocating longitudinal motion inside the reservoir in order to selectably pump the buffer solution into the inner lumen by advancing the plunger or to selectably withdraw the buffer solution from the inner lumen by retracting the plunger.

5. A biosensor system comprising:
   a conduit with an inner lumen with a first end for receiving a target biological fluid and a second end;
   a sensor coupled to the inner lumen remotely from a source of the target biological fluid to detect a target substance; and
   a supply unit for a buffer solution coupled to the inner lumen,
   wherein the supply unit includes a mechanism for advancing the buffer solution along the inner lumen so that the target biological fluid can be purged from an area around the sensor, and wherein, when a measurement is desired, the buffer solution is withdrawn into the supply unit so that the target biological fluid enters the inner lumen and contacts the sensor,
   wherein the buffer solution includes a predetermined calibration concentration of the target substance, wherein the predetermined calibration concentration is less than a predetermined range of concentration of the target substance in the target biological fluid,
   wherein a difference between a measurement of the target substance in the buffer solution and the predetermined calibration concentration identifies a correction which is applied to the measurement for the target biological fluid, and
   wherein the measurement of the target substance in the buffer solution identifies an end-of-life of the sensor when the measurement is less than a threshold.

6. The biosensor system of claim 5 wherein the conduit is comprised of an implantation catheter configured to penetrate a blood vessel, and wherein the target biological fluid is comprised of blood.

7. The biosensor system of claim 5 wherein the buffer solution is comprised of a saline solution.

8. The biosensor system of claim 5 wherein the supply unit includes a reservoir for storing the buffer solution, and wherein the mechanism is comprised of a plunger mounted for reciprocating longitudinal motion inside the reservoir in order to selectably pump the buffer solution into the inner lumen by advancing the plunger or to selectably withdraw the buffer solution from the inner lumen by retracting the plunger.

* * * * *